United States Patent
Wang et al.

(10) Patent No.: US 7,572,898 B2
(45) Date of Patent: Aug. 11, 2009

(54) PROCESS OF MAKING AN ALPHA-ANOMER ENRICHED 2-DEOXY-2,2-DIFLUORO-D-RIBOFURANOSYL SULFONATE AND USE THEREOF FOR MAKING A BETA NUCLEOSIDE

(75) Inventors: Lung-Hu Wang, Shan-Hua (TW); George Schloemer, Shan-Hua (TW); Allen Liu, Shan-Hua (TW)

(73) Assignee: ScinoPharm Taiwan, Ltd., Tainan County (TW)

( * ) Notice: Subject to any disclaimer, the term of this patent is extended or adjusted under 35 U.S.C. 154(b) by 164 days.

(21) Appl. No.: 11/439,664

(22) Filed: May 24, 2006

(65) Prior Publication Data

US 2006/0276638 A1 Dec. 7, 2006

Related U.S. Application Data

(60) Provisional application No. 60/687,593, filed on Jun. 3, 2005.

(51) Int. Cl.
*C07H 15/00* (2006.01)
(52) U.S. Cl. .................... 536/18.5; 536/18.6
(58) Field of Classification Search ............ None
See application file for complete search history.

(56) References Cited

U.S. PATENT DOCUMENTS

| 4,526,988 | A | * | 7/1985 | Hertel ............ 549/313 |
| 5,256,798 | A | | 10/1993 | Chou et al. |
| 5,401,861 | A | * | 3/1995 | Chou ............ 549/476 |
| 5,606,048 | A | | 2/1997 | Chou et al. |

OTHER PUBLICATIONS

Wallner et al. Tetrahedron (2005), vol. 61, pp. 1517-1521.*

* cited by examiner

*Primary Examiner*—Patrick T Lewis
(74) *Attorney, Agent, or Firm*—Cohen Pontani Lieberman & Pavane LLP

(57) ABSTRACT

A process of preparing an alpha-anomer enriched 2-deoxy-2,2-difluoro-D-ribofunanosyl sulfonate, which is useful as an intermediate in the preparation of a beta nucleoside, such as gemcitabine, an anti-tumor agent. A beta-2-deoxy-2,2-difluoro-D-ribofunanosyl sulfonate is heated and converted to an alpha-2-deoxy-2,2-difluoro-D-ribofunanosyl sulfonate in the absence of an effective amount of a sulfonate salt to facilitate the conversion. In addition, an anomeric mixture of an alpha-anomer and a beta-anomer of 2-deoxy-2,2-difluoro-D-ribofunanosyl sulfonate can be dissolved in a mixture of water and a solvent and heated to produce a lactol, which may be further converted to an alpha-anomer enriched 2-deoxy-2,2-difluoro-D-ribofunanosyl sulfonate.

26 Claims, No Drawings

PROCESS OF MAKING AN ALPHA-ANOMER ENRICHED 2-DEOXY-2,2-DIFLUORO-D-RIBOFURANOSYL SULFONATE AND USE THEREOF FOR MAKING A BETA NUCLEOSIDE

RELATED APPLICATIONS

This application claims priority from U.S. Provisional Patent Application Ser. No. 60/687,593 which was filed on Jun. 3, 2005.

BACKGROUND OF THE INVENTION

1. Field of the Invention

The present invention pertains to a process of preparing alpha-anomer enriched 2-deoxy-2,2-difluoro-D-ribofunanosyl sulfonates, which are useful as intermediates in the preparation of beta nucleosides, which are anti-tumor agents. Specifically, the present invention pertains to a process of converting beta-2-deoxy-2,2-difluoro-D-ribofunanosyl sulfonates to alpha-2-deoxy-2,2-difluoro-D-ribofunanosyl sulfonates, which may be further converted to desired beta nucleosides.

2. Description of the Related Art

Stereoselective process for preparing a nucleoside involves stereochemical inversion of a furanose sugar at the anomeric position, therefore when beta-nucleoside is the desired product, an appropriate sugar intermediate enriched in alpha anomer is preferably used as the substrate in the glycosylation reaction. For example, the known substance, gemcitabine, is a nucleoside in the β-configuration and, therefore, it may preferably be prepared by inversion of the center resulting from SN2 displacement of a blocked cytosine on the appropriate sugar sulfonate intermediate in the α-configuration.

Currently known technology results in the preparation of alpha-anomer enriched sulfonate esters by the reaction of a blocked sugar lactol with a sulfonating reagent at low temperatures. The desired alpha-anomer can be crystallized in enhanced purity but in low yield. The remaining material is usually a mixture of alpha and beta anomers from which enriched alpha-anomer can not easily be isolated. Without an effective method of recovering this material and converting it to the desired alpha enhanced anomer, the yield of alpha anomer is low, and the commercial viability of the process is in jeopardy.

U.S. Pat. No. 5,256,798 discloses a process of preparing an alpha-anomer enriched ribofuranosyl sulfonate by treating a beta-anomer ribofuranosyl sulfonate with a source of conjugate anion of a sulfonic acid (i.e., sulfonate salt) at an elevated temperature in an inert organic solvent. However the difficulty of solubilizing the conjugate anion of sulfonic acid in a solvent and the necessity of removal of the solvent and aqueous workup limit the usefulness of this procedure. Therefore there is still a need for a more efficient procedure.

SUMMARY OF THE INVENTION

The present invention provides a process for producing an alpha-anomer enriched ribofunanosyl methanesulfonates of formula (I)

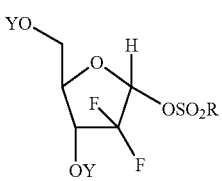

comprising heating a beta-anomer of the formula (II)

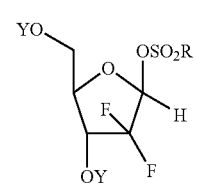

to convert the beta-anomer to the alpha-anomer in the absence of an effective amount of a sulfonate salt to facilitate the conversion of the beta-anomer to the alpha-anomer; wherein each Y is independently selected from hydroxyl protecting groups, and R is an alkyl, substituted alkyl, aryl, or a substituted aryl group.

In addition, the present invention provides a process of making a lactol of formula (III)

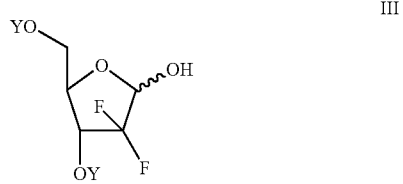

comprising the steps of
a) dissolving a mixture of an alpha-anomer of formula (I) and a beta-anomer of formula (II) in a mixture of an organic solvent, preferably a polar organic solvent, and water;
b) heating the mixture at an elevated temperature to cause the reaction of solvolysis; and
c) diluting the mixture with water and extracting the lactol of Formula (III) with an organic solvent.

The lactol of formula III can be converted to a ribofunanosyl sulfonate, preferably enriched in alpha-anomer of formula (I), by reacting with a sulfonating reagent.

The alpha-anomer of formula I can be caused to react with a nucleobase derivative to prepare a beta-anomer enriched nucleoside of the formula (IV)

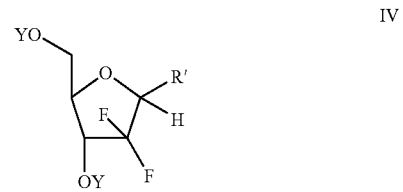

wherein R' is a nucleobase.

DETAILED DESCRIPTION OF THE PRESENTLY PREFERRED EMBODIMENTS

As used herein, the term "alpha/beta mixtures" refers to sulfonate esters of 2-deoxy-2,2-difluoro-D-ribofuranose of formula (I) and (II). It is expressed as a weight/weight ratio or as a percent.

The term "epimerization" refers to the isomerization of the sulfonate esters of formula (I) and (II).

The term "lactol" refers to 2-deoxy-2,2-difluoro-D-ribofuranose of formula (III).

The term "alpha-enriched" or "alpha-enhanced" mixture refers to a mixture with a ratio of alpha and beta anomers greater than 1:1 and includes a substantially pure alpha anomer.

The term "hydrolysis" or "solvolysis" refers to the replacement of the sulfonate ester by an hydroxyl group to form the lactol.

The term "thermal isomerization" refers to the heating of the alpha/beta mixture to convert the beta anomer to the alpha anomer without the addition of a sulfonate salt to facilitate the conversion of the beta-anomer to the alpha-anomer.

The term "alkyl", refers to a straight, cyclic, or branched chain aliphatic hydrocarbon group.

The term "lower alkyl" refers to an alkyl group which contains up to seven carbon atoms such as methyl, ethyl, n-propyl, isopropyl, n-butyl, t-butyl, n-pentyl, n-hexyl, or 3-methylpentyl.

The term "aryl" refers to a carbocyclic or heterocyclic group, such as phenyl, naphythyl, or thienyl.

The term "lower aryl" refers to an aryl group which contains from 6 to 12 carbon atoms such as phenyl, substituted phenyl, naphthyl, etc.

R in the alpha-anomer formula (I) and beta-anomer (II) is preferably a lower alkyl or aryl group.

The term "substituted" refers to the replacement of hydrogen or a common moiety by one or more of the groups such as cyano, halo, carboalkoxy, aryl, nitro, alkoxy, alkyl, and dialkylamino.

The nucleobase (R') employed herein are commonly known to organic chemists and no discussion of their synthesis is necessary. However, in order to be useful in the present glycosylation process, nucleoside derivatives or their tautomeric equivalents bearing amino or hydroxyl groups preferably contain protecting groups, such as primary amino protecting groups (W) and/or hydroxyl protecting groups (Z), depending on the nature of the nucleobase derivative selected. The protecting groups block the hydroxyl or amino groups which may provide competing reaction sites for the beta- or alpha-anomer carbohydrates. The protecting groups are attached to the nucleobase (R'), which is reacted with the alpha-anomer enriched carbohydrate of formulas (I), and are removed subsequent thereto. A procedure for protecting nucleobase derivatives is described in U.S. Pat. No. 4,526,988, the entire content of which is incorporated herein as reference. Likewise, organic chemists can readily select a suitable nucleobase derivative for linking the desired nucleobase (R') to an alpha or beta carbohydrate of formula (I) or (II). For example, U.S. Pat. Nos. 5,426,183 and 4,526,988 disclose a number of nucleobases and nucleobase derivatives. The entire content of U.S. Pat. Nos. 5,426,183 and 4,526,988 is incorporated herein as reference.

For example, nucleobases without protecting groups include the following:

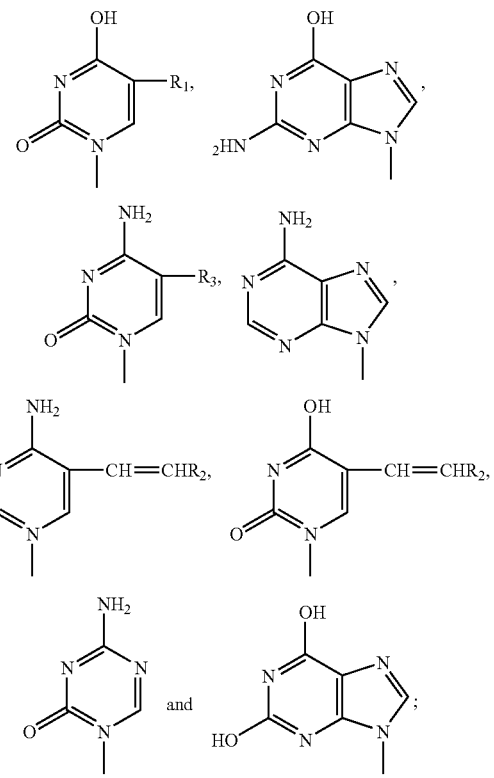

wherein $R_1$ is selected from the group consisting of hydrogen, alkyl, halo, and derivatives thereof; and $R_2$ is selected from the group consisting of hydrogen, alkyl, halo, and derivatives thereof.

Protected nucleobases include, e.g., the following:

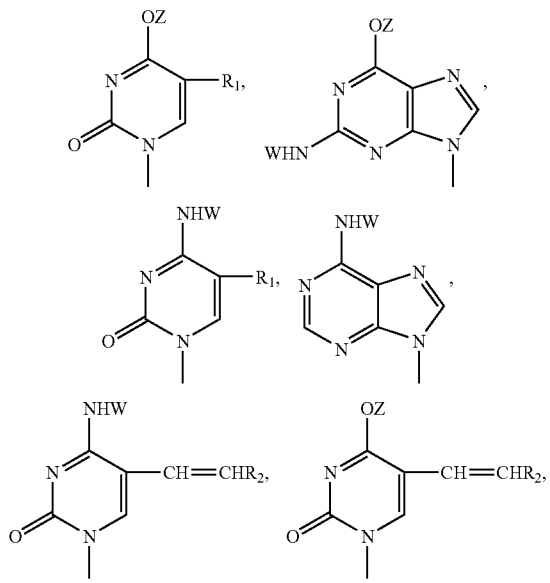

-continued

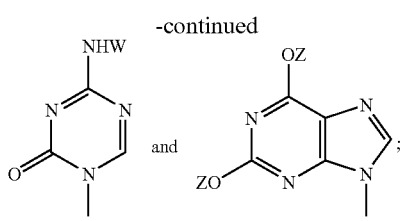
and wherein Z is a hydroxyl protecting group; W is an amino protecting group; $R_1$ is selected from the group consisting of hydrogen, alkyl, halo, and derivatives thereof; and $R_2$ is selected from the group consisting of hydrogen, alkyl, halo, and derivatives thereof.

The suitable nucleobase derivatives include, e.g., the following:

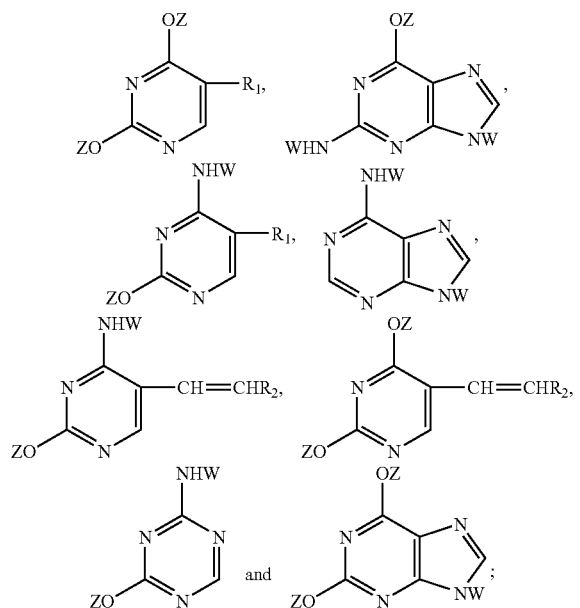

wherein Z is a hydroxyl protecting group; W is an amino protecting group; $R_1$ is selected from the group consisting of hydrogen, alkyl, halo, and derivatives thereof; and $R_2$ is selected from the group consisting of hydrogen, alkyl, halo, and derivatives thereof.

The term "sulfonate salt" refers to a source of conjugate anion of a sulfonic acid, as explained in U.S. Pat. No. 5,256,798, the entire content of which is incorporated herein as reference.

The term "sulfonating reagent" refers to an reagent that can react with the lactol of formula (III) to prepare a sulfonate ester of 2-deoxy-2,2-difluoro-D-ribofuranose of formula (I) or (II). Suitable sulfonating reagents may be selected from the group consisting of arylsulfonyl halides, substituted arylsulfonyl halides, arylsulfonyl anhydrides and substituted arylsulfonyl anhydrides. Substituted arylsulfonyl halides are selected from the group consisting of 2-nitrobenzenesulfonyl chloride, p-cyanobenzenesulfonyl 3-nitrobenzenesulfonyl chloride, 2,4-dinitrobenzenesulfonyl chloride, p-bromobenzenesulfonyl chloride, p-fluorobenzenesulfonyl chloride, 2,4,6-triisopropylbenzenesulfonyl chloride, 2,4,6-trimethylbenzenesulfonyl chloride, p-iodobenzenesulfonyl chloride, p-chlorobenzenesulfonyl chloride, p-methoxybenzenesulfonyl chloride, and p-toluenesulfonyl chloride; preferred are 2-nitrobenzenesulfonyl chloride, 3-nitrobenzenesulfonyl chloride, p-bromobenzenesulfonyl chloride, p-fluorobenzenesulfonyl chloride, and p-chlorobenzenesulfonyl chloride; most preferred is p-bromobenzenesulfonyl chloride. Preferred arylsulfonyl anhydrides are selected from benzene sulfonic acid anhydride and p-bromobenzenesulfonic acid anhydride. Preferred arylsulfonyl halides are selected from benzenesulfonyl chloride and 2-naphthylenesulfonyl chloride; more preferred is benzenesulfonyl chloride.

The term "hydroxyl protecting group" (Y and Z), as used herein, refers to a labile chemical moiety to protect a hydroxyl group against undesired reactions during synthetic procedures. After said synthetic procedure(s) the hydroxyl protecting group as described herein may be selectively removed. The hydroxyl protecting groups are known in the art and are described in Chapter 3 of Protective Groups in Organic Chemistry, McOmie Ed., Plenum Press, New York (1973), and Chapter 2 of Protective Groups in Organic Synthesis, Green, John, J. Wiley and Sons, New York (1981); the entire content of both of these references is incorporated herein as reference. Preferred hydroxyl protecting groups are ester forming groups such as formyl, acetyl, substituted acetyl, propionyl, butynyl, pivaloyl, 2-chloroacetyl, benzoyl, substituted benzoyl, phenoxy-carbonyl, methoxyacetyl; carbonate derivatives such as phenoxycarbonyl, t-butoxycarbonyl ethoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxy-methyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkyl-silyl and 1,1,3,3,-tetraisopropyldisloxanyl; carbamates such as N-phenylcarbamate an d N-imidazoylcarbamate; however more preferred are benzoyl, mono-substituted benzoyl and disubstituted benzoyl, acetyl, pivaloyl, triphenylmethyl ethers, and silyl ether forming groups, especially t-butyldimethylsilyl; while most preferred is benzoyl.

The term "amino protecting group" (W), as used herein, refers to a labile chemical moiety to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, Protective Groups in Organic Synthesis, 3rd edition, John Wiley & Sons, New York (1999), the entire content of which is incorporated herein as reference. Examples of amino protecting groups include, but are not limited to, silyl ether forming groups such as trialkylsilyl, t-butyldialkylsilyl and t-butyldiarylsilyl; carbamates such as t-butoxycarbonyl, benzyloxycarbonyl, 4-methoxybenzyloxycarbonyl, 9-fluorenylmethoxycarbonyl, and 4-nitrobenzyloxycarbonyl; formyl, acetyl, benzoyl and pivalamido; ether forming groups such as methoxymethyl, t-butyl, benzyl, allyl and tetrahydropyranyl; alkylcarboxamides, haloalkylcarboxamides, and arylcarboxamides such as 2-trialkylsilylethoxymethyl, 4-methoxybenzyl, 3,4-dimethoxybenzyl, t-butyl, phthalamido, tetrahydropyranyl, tetrahydrofuranyl, methoxymethyl ether, methoxythiomethyl, trityl, pivalamido, t-butyidimethylsilyl, t-hexyldimethylsilyl, triisopropylsilyl, trichloroethoxycarbonyl, trifluoroacetyl, naphthoyl, formyl, acetyl; sulfonamides such as alkylsulfonamido and arylsulfonamido.

The term "halo" refers to fluoro, chloro, bromo, and iodo.

The term "polar inert solvent", as used herein, refers to a polar solvent which is inert to the reaction conditions. Examples of polar inert solvents include amides, sulfoxides, nitriles, and ethers, more specifically, dimethylsulfoxide, acetonitrile, glyme, diglyme, tetrahydrofuran, dioxane, pyridine, N-methylpyrrolidinone, N,N-dimethylformamide, 1,3-dimethyl-2-imidazolone, N,N-dimethylacetamide, and mixtures thereof; most preferred is N,N-dimethylformamide.

The choice of solvent should allow for some water solubility to carry out the hydrolysis reaction of making the lactol of Formula (III).

The glycosylation reaction between the alpha-anomer of formula (I) and the nucleobase derivative can be carried out by any suitable method, e.g., the method disclosed in U.S. Pat. No. 5,606,048, the entire content of which is herein incorporated as reference. For example, the glycosylation reaction may be carried out at a temperature ranging from about 50° C. to about 100° C., in an inert solvent such as aromatic, haloalkyl, alkoxyl- and halo substitute aromatic solvents. Preferably the inert solvent is a polar inert solvent.

Anomeric mixtures of 2-deoxy-2,2-difluoro-D-ribofuranose sulfonates can be readily synthesized by methods published in the prior art, such as U.S. Pat. Nos. 4,526,988; 4,965,374; and 5,252,756. The entire content of each of these patents is incorporated herein as reference. The temperature of the reaction has been shown to greatly influence the formation of alpha-sulfonate over beta-sulfonate (see U.S. Pat. No. 5,401,861). The use of higher temperatures produces less enhancement of the alpha-sulfonate formation and, therefore, lower yields of enriched alpha-sulfonate after crystallization.

This invention provides several methods of re-enhancing the alpha/beta mixture that remains after crystallization in order to recycle back the re-enhanced mixture to an alpha-sulfonate enhanced product.

The first method takes advantage of the ability to solvolyze a sulfonate back to the lactol in a mixture of a polar organic solvent and water. This is indicated below.

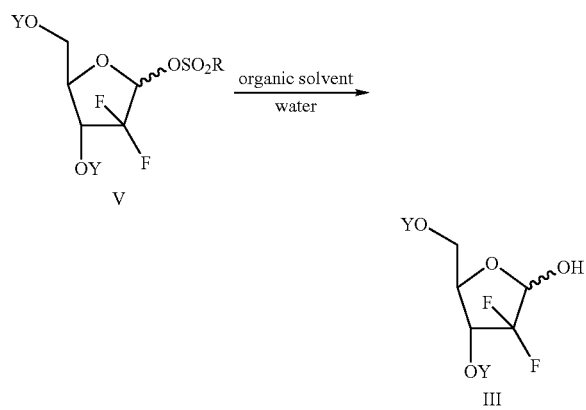

The resulting lactol can then readily be subjected to the sulfonation procedure to produce an alpha-sulfonate, in particular an anomeric mixture enriched in alpha-sulfonate. This cycle greatly increases the yield of enriched alpha-mesylate that can be obtained from the initial lactol. The sulfonation procedure of producing the alpha-sulfonate, in particular the anomeric mixture enriched in alpha-sulfonate, from the lactol, can be any suitable method, such as the low temperature process disclosed in U.S. Pat. No. 5,401,861, the entire content of which is incorporated herein as reference.

The solvolysis occurs by a $SN_1$ mechanism under thermal conditions. A polar, higher boiling non-nucleophilic organic solvent in which water is soluble is preferred. Suitable solvents could be, but not limited to, water soluble ethers, amides, nitriles, and sulfoxides. For a better rate of reaction, a temperature of at least 100° C. is preferred and a temperature range of about 100° C. to about 140° C. is more preferred. Complete conversion of the sulfonate can occur in minutes to hours, and the lactol product can easily be recovered by addition of water and extraction into an organic solvent.

In accordance with one embodiment of the present invention, the process of making the lactol of formula III from the sulfonates of formula V can be carried out as follows: a) dissolving the alpha/beta sulfonate mixture of formula V in a mixture of a water miscible solvent, water, and optionally, a weakly basic material such as carboxylates such as sodium acetate, tertary amines, buffer solutions with pH between 4-9; b) heating the mixture of a) at an elevated temperature until solvolysis is complete; c) diluting the mixture with water and extracting with an organic solvent to yield the lactol of formula (III).

The organic solvent used to extract the lactol may be any solvent not miscible in water such as toluene, methylene chloride, ethyl acetate, etc.

The second method of recovering an alpha-enhanced ribofuranosyl sulfonate proceeds through the direct thermal isomerization of the alpha/beta mixture without the addition of any sulfonate salt used by the process of U.S. Pat. No. 5,256,798.

U.S. Pat. No. 5,256,798 discloses that "heating a solution of 2-deoxy-2,2-difluororibofuranosyl methanesulfonate in an inert organic solvent to 130° C. for extended periods of time does not effect the anomeric configuration of the anomer". Therefore, U.S. Pat. No. 5,256,798 proposes an anomerization process for providing an alpha-anomer enriched ribofuranosyl sulfonate by treating a beta-anomer ribofuranosyl sulfonate with a sulfonate salt at an elevated temperature in an inert solvent.

We have surprisingly discovered that simply heating beta-anomer sulfonate of formula (II) that is essentially free of any solvent and in the absence of any sulfonate salt at an elevated temperature up to about 130° C. readily produces anomeric isomerization. The preferred temperature range is about 90° C. to about 130° C. In fact, this method can be used to prepare enhanced alpha mixtures directly from the mesylation reaction by simply working up the reaction as normal, removing the solvent, heating the residue, adding a suitable organic solvent and crystallizing the enriched alpha sulfonate. After each isolation of the enriched alpha-sulfonate, the residue can be recycled by simply removing the solvent, heating the residue, adding a suitable organic solvent and crystallizing the enriched alpha-sulfonate. In the context of performing this process to produce enhanced alpha mixtures, the condition of essentially free of any solvents means in the presence of a solvent in no amount that would substantially prevent the production of enhanced alpha mixtures.

EXAMPLES

The following examples illustrate specific aspects of the present invention and are not intended to limit the scope thereof in any aspect and should be so construed.

Example 1

Isomerization of an Anomeric Mixture of 2-deoxy-2,2-difluoro-D-ribofuranose Mesylate In a suitable flask is placed 10 grams of 2-deoxy-2,2-difluoro-D-ribofuranose mesylate with a alpha/beta ratio of 1.43. The mixture is heated without solvent for 3 hours at 120° C. to effect isomerization. The mixture is cooled to 75° C. and the HPLC indicated an alpha/beta ratio of approximately 2:1. To this mixture was charged 28 ml of ethyl acetate and 42 ml of heptane and 1 gram of activated carbon. The mixture was stirred 1 hour at 70° C., filtered and cooled to 20° C. A seed crystal of 2-deoxy-2,2-difluoro-D-ribofuranose alpha-mesylate and the mixture was further cooled to 0 C with stirring. After stirring for 2 hours, the product was collected by filtration and the alpha-mesylate was collected. The yield was 2.3 grams of material exhibiting a alpha/beta ratio of 20:1. The solvent can be removed from the filtrate and the isomerization and crystallization process repeated with similar results.

Example 2

Isomerization of 2-deoxy-2,2-difluoro-D-ribofuranose Beta-mesylate to an Mixture Enriched in 2-deoxy-2,2-difluoro-D-ribofuranose Alpha-mesylate A mixture containing a substantial amount of 2-deoxy-2,2-difluoro-D-ribofuranose beta-mesylate (alpha/beta 1:8) was heated in the absence of any solvent at 130° C. for 3 hours. HPLC analysis indicated an alpha/beta ratio of 1.7:1.

Example 3

Hydrolysis of Anomeric Mixture of 2-deoxy-2,2-difluoro-D-ribofuranose Mesylate To a flask containing 50 grams of 2-deoxy-2,2-difluoro-D-ribofuranose mesylate anomeric mixture (alpha/beta 1:1) was added 250 ml DMF and 12 ml water. The mixture was heated at reflux for 4 hours at which time analysis indicated that all the mesylate had been converted back to 2-deoxy-2,2-difluoro-D-ribofuranose. The mixture is diluted with water and extracted with ethyl acetate. The solution is washed with water and the solvent is removed. Toluene is added and distilled to produce an oil (48 grams) which can be used in a low temperature reaction (e.g., the low temperature process disclosed in U.S. Pat. No. 5,401,861) to produce a 2-deoxy-2,2-difluoro-D-ribofuranose alpha-mesylate enriched product.

The present invention is not limited by the embodiments described above which are presented as examples only but can be modified in various ways within the scope of protection defined by the appended patent claims.

What is claimed is:

1. A process for producing an alpha-anomer ribofuranosyl sulfonate of formula (I)

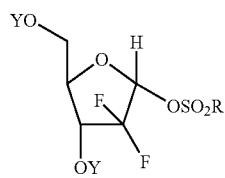

from a beta-anomer of ribofuranosyl sulfonate of formula (II)

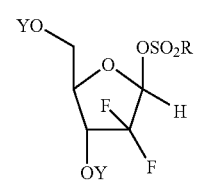

comprising heating the beta-anomer that is essentially free of a solvent at an elevated temperature to convert the beta-anomer to the alpha-anomer in the absence of an effective amount of a sulfonate salt to facilitate the conversion of the beta-anomer to the alpha-anomer; wherein each Y is independently selected from hydroxyl protecting groups, and R is an alkyl, substituted alkyl, aryl, or a substituted aryl group.

2. The process of claim 1 wherein the elevated temperature is up to about 130° C.

3. The process of claim 1 wherein the elevated temperature is from about 90° C. to about 130° C.

4. The process of claim 1 wherein R is a lower alkyl or aryl group.

5. The process of claim 1 wherein R is methyl.

6. The process of claim 1 wherein R is benzoyl or substituted benzoyl.

7. The process of claim 1 wherein the produced alpha-anomer is present in an alpha-anomer enriched mixture, and the heated beta-anomer is present in an anomeric mixture.

8. A process of making a nucleoside of formula (IV)

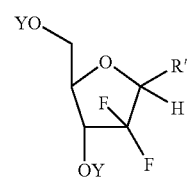

comprising:

a) heating a beta-anomer of formula (II) that is essentially free of a solvent

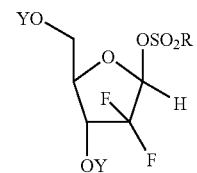

at an elevated temperature to convert the beta-anomer to an alpha-anomer of formula (I)

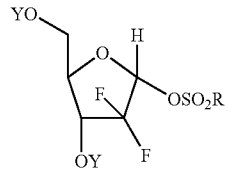

in the absence of an effective amount of a sulfonate salt to facilitate the conversion of the beta-anomer to the alpha-anomer; and b) reading the alpha-anomer with a nucleobase derivative to prepare the nucleoside;

wherein each Y is independently selected from hydroxyl protecting groups, R is an alkyl, substituted alkyl, aryl, or a substituted aryl group; and R' is a nucleobase.

9. The process of claim 8 wherein R' is any of the following:

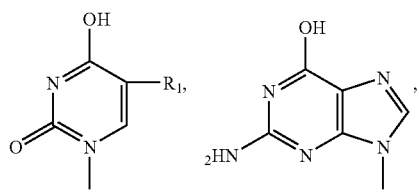

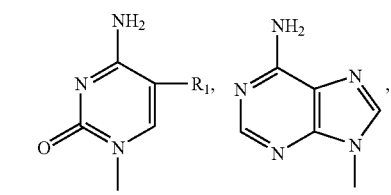

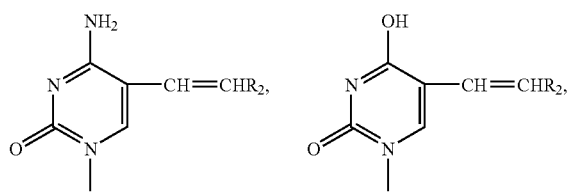

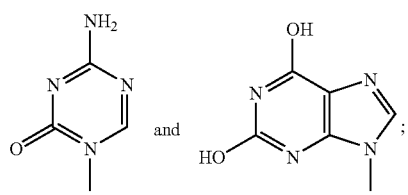

wherein $R_1$ is selected from the group consisting of hydrogen, alkyl, halo, and derivatives thereof; and $R_2$ is selected from the group consisting of hydrogen, alkyl, halo, and derivatives thereof.

10. The process of claim 8 wherein R' is any of the following:

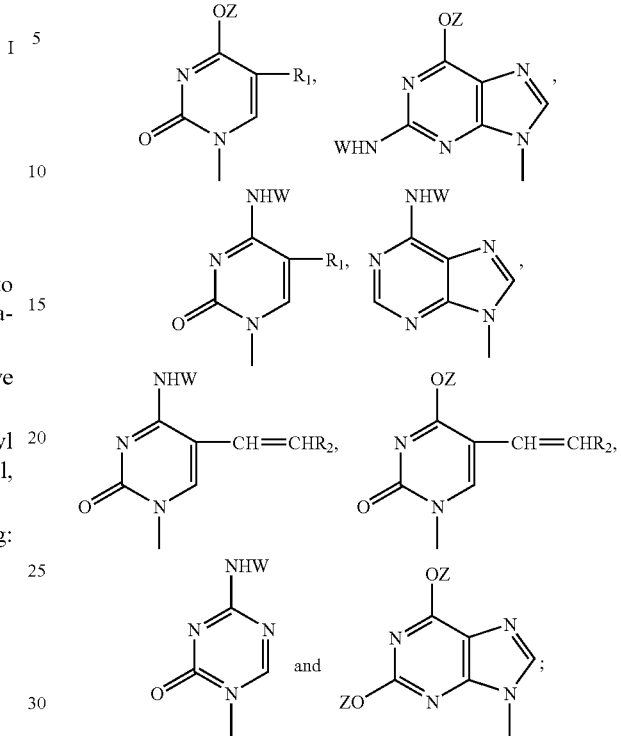

wherein Z is a hydroxyl protecting group; W is an amino protecting group; $R_1$ is selected from the group consisting of hydrogen, alkyl, halo, and derivatives thereof; and $R_2$ is selected from the group consisting of hydrogen, alkyl, halo, and derivatives thereof.

11. The process of claim 8 wherein the nucleobase derivative is selected from the following:

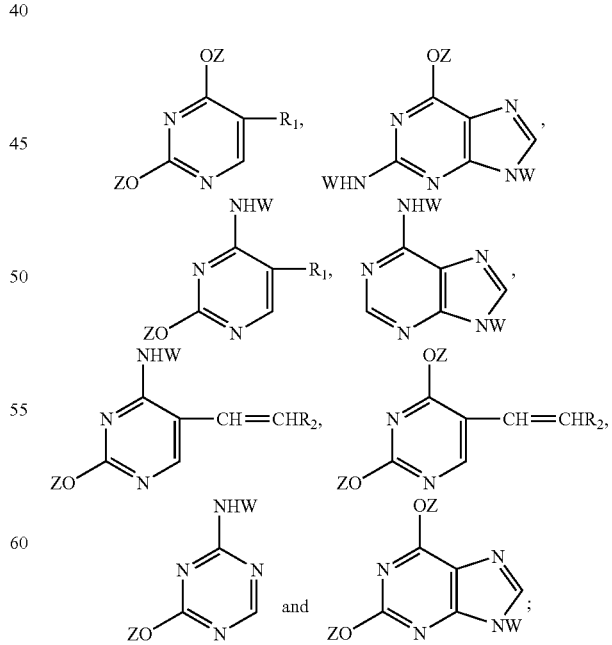

wherein Z is a hydroxyl protecting group; W is an amino protecting group; $R_1$ is selected from the group consisting of hydrogen, alkyl, halo, and derivatives thereof; and R$_2$ is selected from the group consisting of hydrogen, alkyl, halo, and derivatives thereof.

12. The process of claim 8 wherein nucleoside is gemcitabine.

13. A process of making a lactol of formula (III) comprising the steps of:
   a) dissolving an anomeric mixture of formula (V) in a mixture of a polar organic solvent and water at a pH of between 4-9,

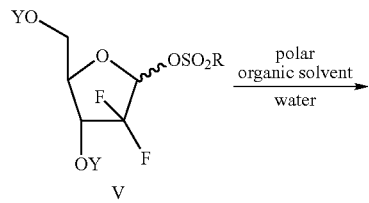
V

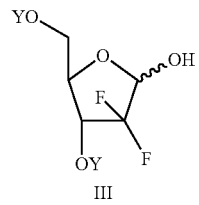
III wherein each Y is independently selected from hydroxyl protecting groups, and R is an alkyl, substituted alkyl, awl, or a substituted awl group;
   b) heating the mixture at an elevated temperature to cause the reaction of solvolysis to obtain a latol of formula III as shown above; and
   c) diluting the mixture with water and extracting the lactol with a water-immiscible organic solvent.

14. The process of claim 13 wherein the elevated temperature is at least 100° C.

15. The process of claim 13 wherein the elevated temperature is from about 100° C. to about 140° C.

16. The process of claim 13 wherein the polar organic solvent is selected from amides, sulfoxides, nitriles, and ethers.

17. The process of claim 13 wherein the polar organic solvent is N,N-dimethylformamide.

18. The process of claim 13 wherein Y is benzoyl or substituted benzoyl and R is methyl.

19. The process of claim 13 wherein the lactol is reacted with a sulfonating reagent to produce an alpha anomer of (I)

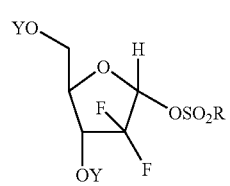
I wherein each Y is independently selected from hydroxyl protecting groups, and R is an alkyl, substituted alkyl, aryl, or a substituted aryl group.

20. The process of claim 19 wherein the produced alpha-anomer is present in an alpha-anomer enriched mixture.

21. The process of claim 19 wherein the alpha anomer of formula (I) is reacted with a nucleobase derivative to produce a nucleoside.

22. A process of making a nucleoside of formula (IV)

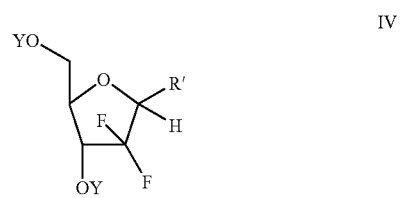
IV wherein each Y is independently selected from hydroxyl protecting groups, R' is a nucleobase; comprising:
   a) dissolving an anomeric mixture of formula (V) in a mixture of polar organic solvent and water at a pH of between 4-9,

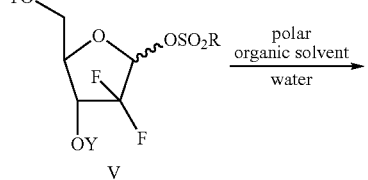
V

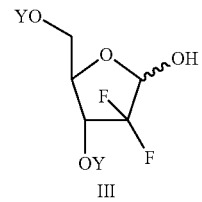
III wherein each Y is independently selected from hydroxyl protecting groups, and R is an alkyl, substituted alkyl, aryl, or a substituted aryl group;
   b) heating the mixture at an elevated temperature to cause a solvolysis reaction to obtain a lactol of formula (III) as shown above; and
   c) diluting the mixture with water and extracting the lactol of formula (III) with a water-immiscible organic solvent;
   d) reacting the lactol of formula (III) with a sulfonating reagent to produce an alpha anomer of formula (I)

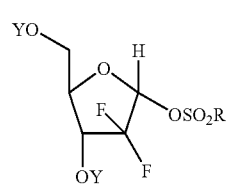
I wherein each Y is independently selected from hydroxyl protecting groups, and R is an alkyl, substituted alkyl, aryl, or a substituted aryl group; and e) reacting the alpha anomer of formula (I) with a nucleoside derivative to prepare the nucleoside.

23. The process of claim 22 wherein the produced alpha-anomer of formula (I) is present in an alpha-anomer enriched mixture.

24. The process of claim 22 wherein R' is any of the following:

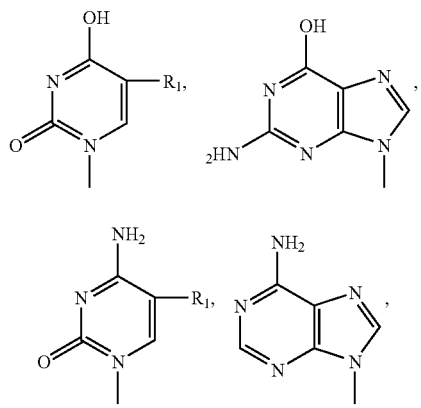

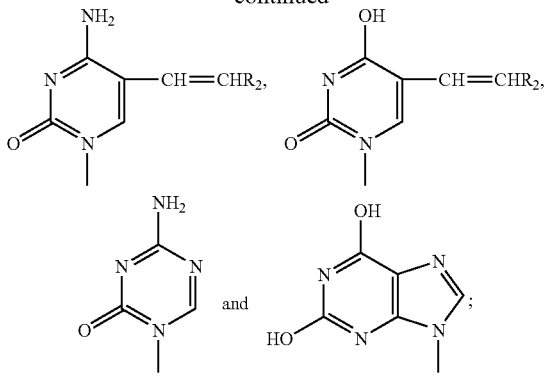

wherein $R_1$ is selected from the group consisting of hydrogen, alkyl, halo, and derivatives thereof; and $R_2$ is selected from the group consisting of hydrogen, alkyl, halo, and derivatives thereof.

25. The process of claim 22 wherein the nucleoside is gemcitabine.

26. The process of claim 22 wherein Y is benzoyl or substituted benzoyl.

* * * * *